United States Patent

Clayton et al.

[11] Patent Number: 5,351,678
[45] Date of Patent: Oct. 4, 1994

[54] ENDOSCOPE SCOPE ASSEMBLY FOR FULL HEMISPHERE VIEW

[75] Inventors: John B. Clayton, Reno, Nev.; Darryl J. Bornhop, Truckee, Calif.; George H. Middle, Reno, Nev.

[73] Assignee: Citation Medical Corporation, Reno, Nev.

[21] Appl. No.: 938,827

[22] Filed: Sep. 1, 1992

[51] Int. Cl.[5] ............................................. A61B 1/06
[52] U.S. Cl. ............................................. 128/6; 128/4
[58] Field of Search ........................ 128/3, 4, 6, 7, 8; 606/1; 604/264

[56] References Cited

U.S. PATENT DOCUMENTS

| | | |
|---|---|---|
| 4,138,192 | 2/1979 | Yamasita . |
| 4,253,448 | 3/1981 | Terada . |
| 4,589,404 | 5/1986 | Barath et al. . |
| 4,590,923 | 5/1986 | Watanabe . |
| 4,607,622 | 8/1986 | Fritch et al. . |
| 4,620,769 | 11/1986 | Tsuno . |
| 4,736,733 | 4/1988 | Adair . |
| 4,754,328 | 6/1988 | Barath et al. . |
| 4,755,873 | 7/1988 | Kobayashi . |
| 4,762,120 | 8/1988 | Hussein . |
| 4,782,819 | 11/1988 | Adair . |
| 4,784,117 | 11/1988 | Miyazaki ............................... 128/4 |
| 4,844,071 | 7/1989 | Chen et al. . |
| 4,865,029 | 9/1989 | Pankratov . |
| 4,867,138 | 9/1989 | Kubota et al. . |
| 4,911,148 | 3/1990 | Sosnowski et al. ................... 128/7 X |
| 4,920,961 | 5/1990 | Grossi et al. . |
| 4,924,851 | 5/1990 | Ognier et al. ....................... 604/264 X |
| 4,926,860 | 5/1990 | Stice et al. ......................... 604/264 X |
| 4,947,245 | 8/1990 | Ogawa et al. . |
| 5,005,943 | 4/1991 | Fort . |
| 5,167,645 | 12/1992 | Castillo .............................. 604/264 X |
| 5,188,093 | 2/1993 | Lafferty et al. ........................... 128/6 |
| 5,207,694 | 5/1993 | Broome ................................. 606/1 X |
| 5,217,466 | 6/1993 | Hasson ................................. 606/1 X |

FOREIGN PATENT DOCUMENTS

| | | |
|---|---|---|
| 0305170 | 3/1989 | European Pat. Off. . |
| 0369937 | 5/1990 | European Pat. Off. . |
| 0498114A1 | 8/1992 | European Pat. Off. . |
| 9203963 | 3/1992 | World Int. Prop. O. ............... 128/6 |

Primary Examiner—Richard J. Apley
Assistant Examiner—Karen A. Jalbert
Attorney, Agent, or Firm—Nydegger & Associates

[57] ABSTRACT

A scope assembly for an endoscope adapted for use with a portal cannula to provide a generally hemispherically shaped field of view within the body. The scope assembly includes a guiding cannula adapted for rotation within the portal cannula. A distal end of the guiding cannula is bent or offset from a longitudinal axis of the scope assembly. A bendable scope is mounted within the guiding cannula and is adapted for rotation within the guiding cannula. A GRIN lens located at a distal or viewing end of the bendable scope is also offset from the longitudinal axis of the bendable scope such that upon rotation of the guiding cannula or bendable scope a generally hemispherically shaped field of view is scanned.

20 Claims, 3 Drawing Sheets

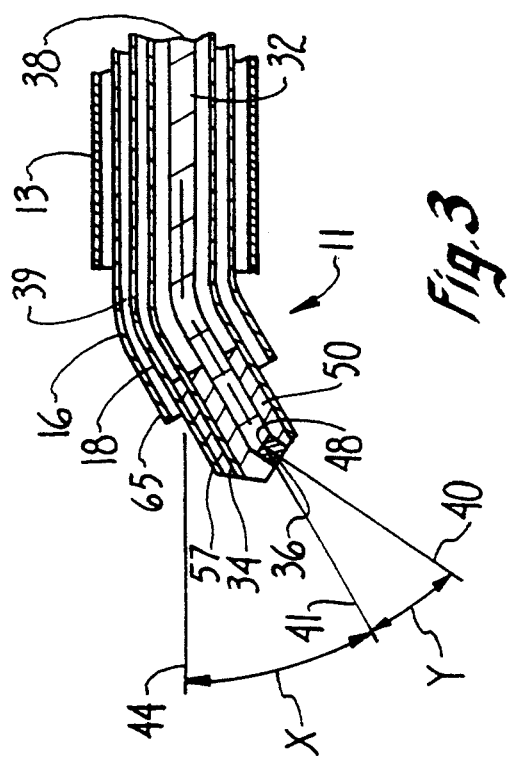
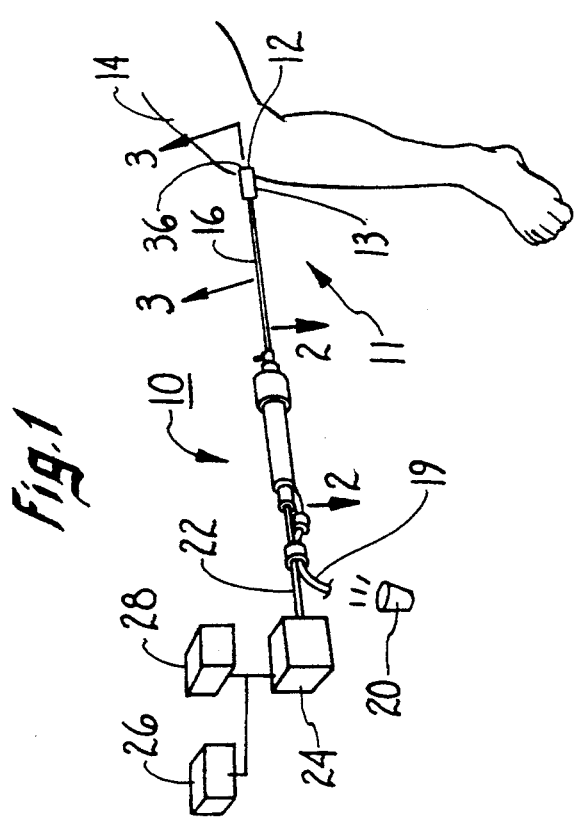
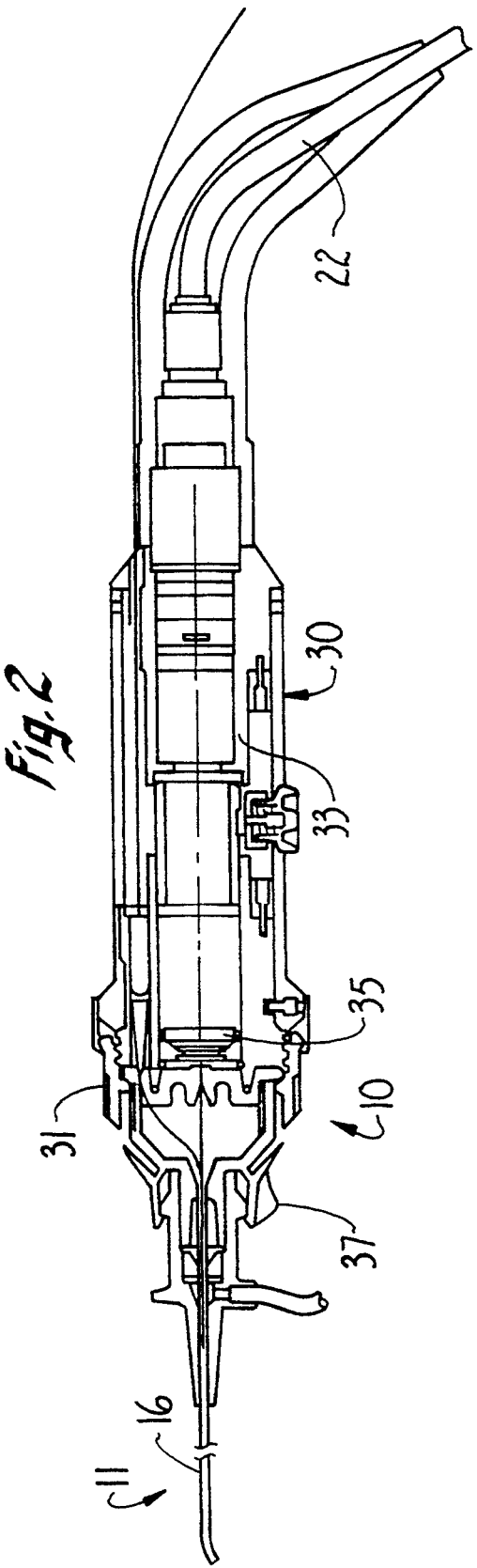

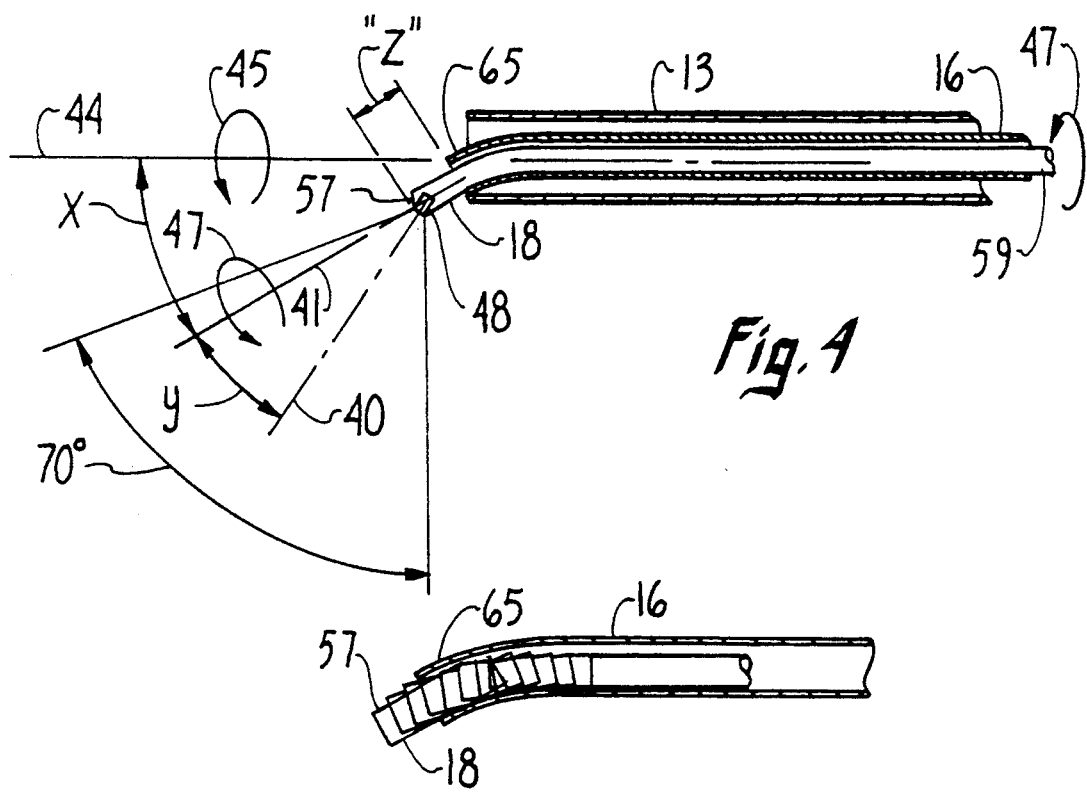
Fig. 4
Fig. 6
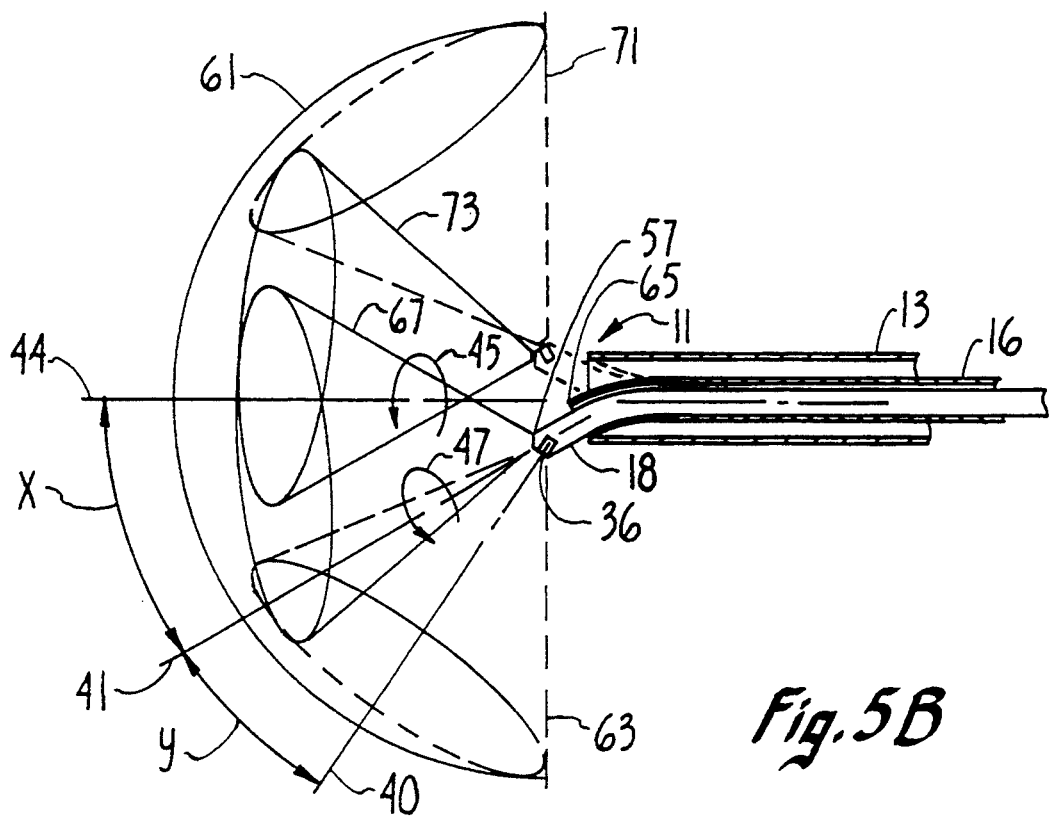
Fig. 5B

ENDOSCOPE SCOPE ASSEMBLY FOR FULL HEMISPHERE VIEW

TECHNICAL FIELD

The present invention relates generally to medical devices and more particularly to endoscopes. The present invention is particularly although not exclusively related to an improved scope assembly for endoscopes such as arthroscopes adapted to provide a full hemispherically shaped field of view within the body.

BACKGROUND OF THE INVENTION

Modern surgical techniques which are relatively non-invasive have been recently developed for viewing and performing different medical procedures to the interior structure of body parts. Medical instruments for carrying out these procedures are known generally as endoscopes and specifically include arthroscopes, laproscopes, spinalscopes, esophagoscopes and others. These instruments typically include a scope which is inserted into the body part to be examined. With an arthroscope, for example, the scope is connected to a camera assembly and the camera assembly in turn is connected to a video display for generating a picture of the interior structure of a joint. Consequently, the operator of the arthroscope is able to view, in real-time, the interior structure of the joint as the scope is moved within the joint. By viewing the internal structure of the joint, a diagnosis of the joint's potential maladies can be made and appropriate treatment prescribed.

In constructing medical endoscopes one requirement is that the scope of the endoscope be relatively small. A small sized scope helps to reduce the size of an entry site into the body (i.e. joint) and also helps to minimize trauma within the body by insertion of the scope.

Coincident with the requirement of a small size, is the requirement that the probe provide as large a field of view as possible within the body. If the scope can be constructed to provide a large field of view within the body, then movement of the scope within the body can be minimized and trauma reduced accordingly.

For this reason endoscopes are often constructed with a scope adapted to provide a wide angle field of view. As an example, this may be accomplished using a viewing lens at a distal end of the scope that possesses a relatively large numerical aperture (N.A.). In addition, some scopes may be constructed with a viewing axis that is angled or oblique with respect to a longitudinal axis of the scope. This angle may be preset (i.e. 30°, 70° and 90°) to facilitate viewing of a particular body structure (i.e. knee, shoulder). With an offset viewing axis, the scope can be rotated within the joint to sweep a field of view.

In order to provide such an offset viewing axis, some endoscopes are constructed with a scope assembly having an arrangement of lens and prisms. U.S. Pat. No. 4,138,192 to Yamasita for instance, discloses such a scope assembly having an optical system that is constructed with an oblique viewing axis.

In general, the construction of this type of endoscope is relatively complicated and expensive. In addition, the scope assembly of such an endoscope may be relatively large or difficult to move within the body. Moreover, because of the expense of the scope assembly, the scope assembly must be reused and sterilized after each use. In view of the possibility of disease transmission between patients, endoscopes that utilize a disposable scope assembly have been introduced in recent years. In general, these disposable scopes are safer and easier to use than endoscopes having a scope assembly that must be sterilized after each use.

There is then a need in the medical field for a relatively inexpensive scope assembly for endoscopes that can provide a large field of view within the body. Further there is a need for such a scope assembly for endoscopes that is of a relatively simple construction that is disposable after a single use.

Accordingly it is an object of the present invention to provide an endoscope scope assembly that provides a full hemispherically shaped field of view within the body. It is another object of the present invention to provide such an endoscope scope assembly having a relatively small distal end for insertion into the body such that trauma to the body is minimized. It is a further object of the present invention to provide such an endoscope scope assembly that is disposable. It is a further object of the present invention to provide a scope assembly for such an endoscope that is relatively inexpensive to manufacture and easy to use yet provides an increased field of view within the body with an acceptable image quality.

SUMMARY OF THE INVENTION

In accordance with the present invention an improved scope assembly for endoscopes adapted to provide a full hemispherically shaped field of view within the body is provided. In an illustrative embodiment of the invention the scope assembly is for an arthroscope. It is to be understood, however, that the inventive concepts disclosed herein can be used in the construction of other types of medical endoscopes, such as spinalscopes, laproscopes, esophagoscopes and others, and in the construction of the scope assemblies for medical instruments other than endoscopes.

The improved endoscope scope assembly, generally stated, includes a guiding cannula and a bendable scope mounted within the guiding cannula. The guiding cannula is adapted to be inserted into an outer cannula which is termed herein the portal cannula. The portal cannula is a stationary member that is inserted into the body part to be examined (i.e. joint, intestine, esophagus, etc.). The guiding cannula is rotatable within the portal cannula.

The bendable scope is adapted to illuminate the body part and return a visual image. The bendable scope is rotatable within the guiding cannula. The distal or viewing end of the bendable scope extends a distance past the distal end of the guiding cannula so that the guiding cannula does not interfere with the path of light into the image guide of the bendable scope. The distal end of the guiding cannula is bent with respect to a longitudinal axis of the scope assembly to provide an angled or oblique guide for the distal or viewing end of the bendable scope. In addition, the distal or viewing end of an image guide within the bendable scope is offset with respect to a longitudinal axis of the scope assembly to compound the offset of the viewing axis. This construction allows the guiding cannula to be rotated within the portal cannula and the bendable scope to be rotated within the guiding cannula to scan a full hemispherically shaped field of view within the body.

In an illustrative embodiment for an arthroscope the scope assembly is disposable and is removably attached to a hand held housing. A camera assembly is also mounted within the housing for focusing an image from the bendable scope. An externally mounted camera control unit controls operation of the camera assembly. In addition, the camera control unit can control a CRT or other visual display device to display an image of the internal structure of the body part.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts.

FIG. 1 is a perspective view of a portable arthroscope having a scope assembly constructed in accordance with the present invention being used to examine a joint of a patient;

FIG. 2 is a schematic cross-sectional view of the arthroscope taken along section line 2—2 of FIG. 1;

FIG. 3 is a cross-sectional view of the viewing end of the scope assembly and portal catheter taken along section line 3—3 of FIG. 1;

FIG. 4 is a schematic view of the distal or viewing end of the scope assembly located within the portal catheter and showing the geometrical locations of the guiding cannula and bendable scope of the scope assembly;

FIGS. 5B is a schematic view of the distal or viewing end of scope assembly constructed in accordance with the invention showing movement of the guiding cannula and bendable scope to provide a generally hemispherically shaped field of view; and FIG. 6 is a schematic view illustrating further details of the construction of the viewing end of the scope assembly.

DESCRIPTION OF PREFERRED EMBODIMENTS

Figure 5A:
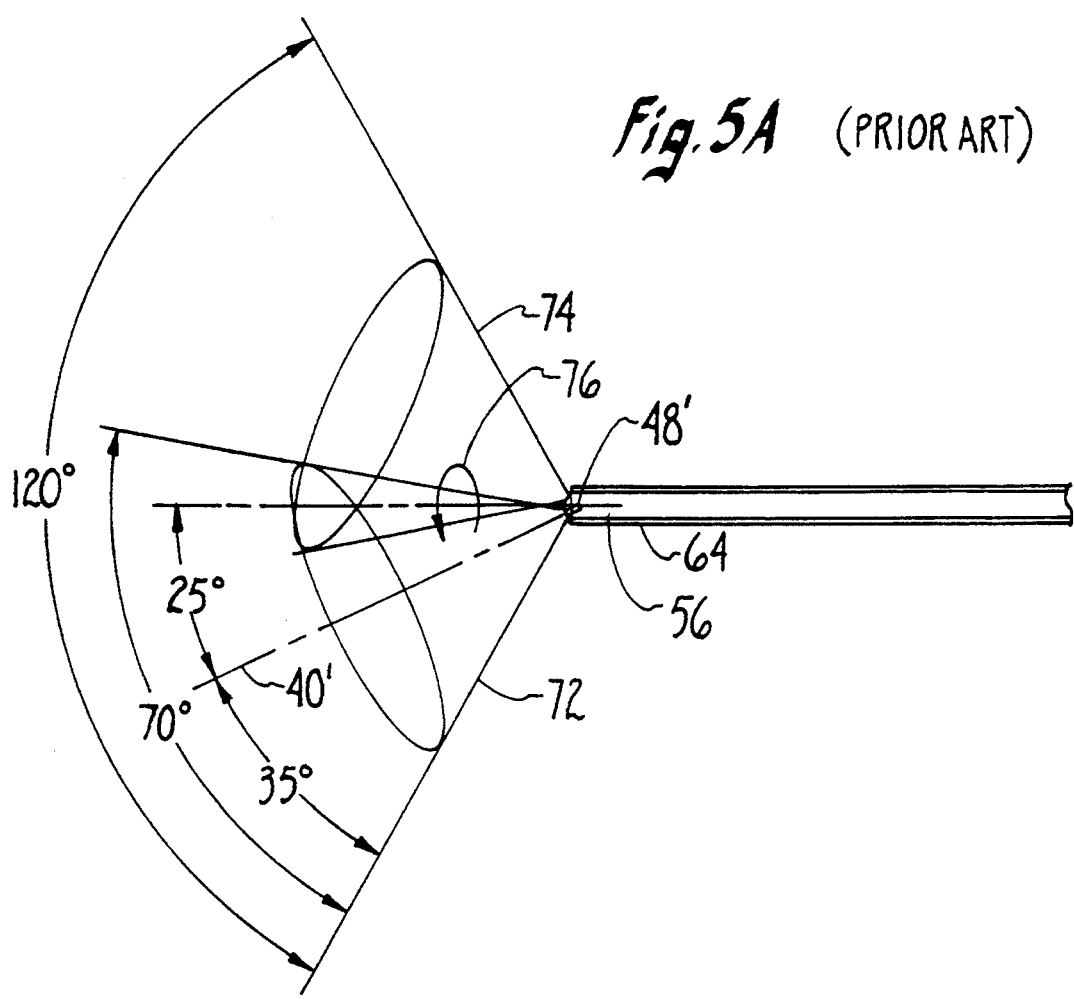
FIG. 5A is a schematic view illustrating a field of view of a prior art endoscope.

The present invention is directed to an improved scope assembly for constructing medical instruments such as arthroscopes. The invention is described herein in connection with a portable arthroscope. The present invention is adapted to provide a full hemispherically shaped field of view within the body for such an arthroscope and for other endoscopes and medical instruments.

With reference to FIG. 1 an arthroscope generally designated 10 includes a scope assembly generally designated 11 that is inserted at an entry site 12 into a knee 14 of patient to examine the internal structure of the knee 14. The scope assembly generally designated 11 includes a guiding cannula 16 and a bendable scope 18 (FIG. 3) rotatably mounted within the guiding cannula 16 and free to rotate within the guiding cannula 16. In addition, a portal cannula 13 is placed into the entry site 12 to provide access for the guiding cannula 16 and bendable scope 18, of the arthroscope 10 to the site within the knee 12 to be examined. Depending on the body part to be examined, the portal cannula 13 may be a relatively short stationary cannula. Importantly, the guiding cannula 16 is rotatable within the portal cannula 13.

The arthroscope 10 is in light communication via optical line 19 to a lamp 20 (e.g. metal halide). The arthroscope 10 is electrically connected via line 22 to a camera control unit 24. Camera control unit 24 can in turn be electrically connected to a cathode ray tube (CRT) 26 and a video camera recorder (VCR) 28, for respectively displaying and recording a video image of the internal structure of the knee 14.

With reference to FIG. 2 the arthroscope 10 also includes a hand held housing 30. The scope assembly 11 is removably attached to the housing 30 using a cap-like connector 31. The guiding cannula 16 is removably attached to the scope assembly 11 using a clamp-like connector 37. The arthroscope 10 also includes focusing optics 35 and a camera assembly 33 mounted within the housing 30 for processing an image received from the scope assembly 11.

With reference to FIG. 3, a distal or viewing end of the improved scope assembly 11 of the arthroscope 10 is shown in detail. As previously stated the scope assembly 11 includes the guiding cannula 16 and the bendable scope 18 mounted within the guiding cannula 16. The bendable scope 18, generally stated, is adapted to illuminate the internal body structure to be examined and to return a visual image of the body structure to the focusing optics 35 (FIG. 2). The guiding cannula 16, generally stated, is adapted to bend the distal or viewing portion of the bendable scope 18 to a pre-set angle to provide an offset viewing axis for the bendable scope 18. In addition the guiding cannula 16 provides a conduit 39 for the introduction of fluid into the body structure. Specifically the conduit 39 is formed by an annular area formed between the I.D. of the guiding cannula 16 and the O.D. of the bendable scope 18.

As shown in FIG. 3, a distal or viewing end 65 of the guiding cannula 16 is bent or offset from a longitudinal axis 44 of the scope assembly 11. A distal or viewing end 57 of the bendable scope 18 follows the shape of the bent distal end 65 of the guiding cannula 16, and extends from the bent distal end 65 of the guiding cannula 16 along an oblique distal axis 41. Distal axis 41 of the guiding cannula 16 is situated at an angle "x" with respect to the longitudinal axis 44 of the guiding cannula 16.

In addition to the oblique distal axis 41 provided by the bent viewing end 57 of the bendable scope 18, a (GRIN) rod 48 located at a viewing end of an image guide 32 mounted within bendable scope 18 is also offset. Stated differently the gradient refractive index (GRIN) rod 48 is bonded to the image guide 32 at an offset viewing angle with respect to oblique distal axis 41. By way of example, the GRIN rod 48 may be a type of internally-refractive lens made of thallium doped glass. The length of the GRIN rod 48 establishes the focusing characteristics which are appropriate for the particular application of the arthroscope 10.

With this arrangement, the distal end 36 (i.e. viewing end) of the GRIN rod 48 of the image guide 32 is situated at an oblique or offset angle "y" with respect to the oblique distal axis 41. This forms an offset viewing axis 40. In addition, with this arrangement rotation of the bendable scope 18 within the guiding cannula 16 by manipulation of the guiding cannula 16 and clamp connector 37 (FIG. 2), allows the GRIN rod 48 of the image guide 32 to sweep an enlarged field of view. Moreover, rotation of the guiding cannula 16 within the portal cannula 13 allows the GRIN rod 48 of the image guide 32 to sweep an even larger field of view. This dual rotation of the guiding cannula 16 within the portal cannula 13 and of the bendable scope 18 within the guiding cannula 16 can be used to provide a full hemispherically shaped field of view.

By way of illustration and not limitation, a suitable angle "x" between the longitudinal axis 44 of the guiding cannula 16 and the distal axis 41 of the guiding cannula 16 has been determined to be about 30 degrees. A suitable angle "y" of the viewing axis 40 with the distal axis 41 has been determined to be about 25 degrees. The total angle of the offset is therefore 55°.

Still referring to FIG. 3, the bendable scope 18 in addition to the image guide 32 and GRIN rod 48 includes a plurality of optical illumination fibers 34 which are positioned within the bendable scope 18 around the image guide 32. Preferably, both image guide 32 and illuminating fibers 34 are optical fibers which have relatively large numerical apertures (NA). The optical illumination fibers 34 are coupled to the light source 20 (FIG. 1) and function to illuminate the interior structure of the body. The image guide 32 and illumination fibers 34 are embedded in an epoxy material 50 at the viewing end 57 of the bendable scope 18. Since such epoxy material 50 is relatively brittle, it only extends a short distance into the bendable scope 18. This permits the bendable scope 18 to be manipulated through and rotated within the guiding cannula 16.

More specifically and with reference to FIG. 6, the bendable scope 18 must be bendable enough to enable the distal end 57 of the bendable scope 18 to be pushed through guided by the bent distal end 65 of the guiding cannula 16. As an example the bendable scope 18 may include a flexible outer tubing (i.e. metal, plastics, polyamide) and just the distal ends of the image guide 32 and illuminating fiber 34 may be embedded within an epoxy material 50 within this outer tubing. A required flexibility of the bendable scope 18 for passing through the bent distal end 65 of the guiding cannula 64 is indicated schematically in FIG. 6 by the segmented structure.

Referring now to FIG. 4 a schematic diagram illustrating further details of construction for the scope assembly 11 is shown. As previously stated, the guiding cannula 16 can rotate 360 degrees within the portal cannula 13 as indicated by arrow 45. This movement is accomplished by rotation of the hand held housing 30 (FIG. 2) of the arthroscope 10. In addition, the bendable scope 18 can rotate within the guiding cannula 16 as indicated by arrow 47. Stated differently, as a proximal end 59 of the bendable scope 18 is rotated, as indicated by arrow 47' the distal end 57 of the bendable scope 18 also rotates as indicated by arrow 47 while being bent by the bent distal end 65 of the guiding cannula 16. The bendable scope 18 must thus be bendable enough to rotate and bend at its distal end 57. It can be seen from FIG. 4 that, where the guiding cannula 16 is straight except for the bend at its distal end 65, it constrains the scope 18 to bend only at its distal end 57. The amount of rotation of the bendable scope 18 within the guiding cannula 16 is dependent on the construction of the bendable scope 18 and may be up to 360°. In an illustrative embodiment, the bendable scope 18 is adapted to rotate within the guiding cannula 16 through an angle of about 270°.

Still referring to FIG. 4 the viewing or distal end 57 of the bendable scope 18 also extends past the distal end 65 of the guiding cannula 16 by a distance "Z". This distance is generally small to enhance lens cleaning and for safety reasons. In general, however, this geometry places the viewing end 57 of the bendable scope 18 and particularly the GRIN rod 48 out of and away from the guiding cannula 16. A path of light from the body into the GRIN rod 48 is therefore unobstructed by the guiding cannula 16.

Referring now to FIGS. 5A and 5B, the mechanics of the field of view obtained by the bendable scope 56 can be explained. For simplicity FIG. 5A illustrates a prior art arrangement in which a guiding cannula 64 and a scope 56 of an endoscope are formed without a bent distal end but with the viewing axis 40' offset by 25 degrees by offset placement of the GRIN rod 48' of an image guide of the scope 56. By selection of a GRIN rod 48' having appropriate optical characteristics, a generally conical shaped field of view 72 is scanned by the GRIN rod 48'. The angle and size of this conically shaped field of view is determined largely by the N.A. of the GRIN rod 48'. As an example, this conical shaped field of view may be formed with a total conical angle of about 70 degrees (i.e. 35 degrees on each side of viewing axis 40'). Similarly, rotation of the scope 56 by 180° as indicated by arrow 76 produces a conical field of view 74. The total field of view is thus 120 degrees.

This type of viewing arrangement as shown in FIG. 5A, will be produced by a generally straight prior art scope having an offset viewing axis. By bending or offsetting the viewing axis 40' another thirty degrees, using a bent guiding cannula 16 as disclosed herein, another sixty degrees can be swept (i.e. 30 degrees on each side of the viewing axis 40). With the present arrangement a full hemispherically shaped field of view can be achieved.

A resultant generally hemispherically shaped field of view obtainable by an endoscope such as the presently disclosed arthroscope 10 is shown in FIG. 5B and is designated as 61. This hemispherically shaped field of view 61 can be obtained by rotating the bendable scope 18 within the guiding cannula 16 as indicated by arrow 47 and by rotating the guiding cannula 16 within the portal cannula 13 as indicated by arrow 45. The guiding cannula 16 is rotated within the portal cannula 13 by rotation of the hand-held housing 30 (FIG. 2) of the arthroscope 10. The bendable scope 18 is rotated by manipulation of the clamp like connector 37 such that the bendable scope 18 is rotated relative to the guiding cannula 16.

As with the prior explanation in connection with FIG. 5A, the stationary field of view of the arthroscope 10 at any position of the bendable scope 18 and guiding cannula 16 is generally conical in shape. As an example in FIG. 5B at a lowermost orientation of the bendable scope 18, a conically shaped field of view 63 outlined in dotted lines is provided. Rotation of the bendable scope 18 as indicated by arrow 47 moves the viewing end 36 of the bendable scope 18 through a donut shaped swath. If the bendable scope 18 is rotated 180° within the guiding cannula 16 a conically shaped field of view 67 shown in solid lines can be provided. This is essentially the 120 degree field of view described in FIG. 5A.

With the present double offset arrangement for the viewing axis 40, however, the guiding cannula 16 can also be rotated to increase this field of view by another 60 degrees. As an example, the guiding cannula 16 can be rotated as indicated by arrow 45 to reorient the viewing end 36 of the bendable scope 18 as shown in phantom. A 180 degree rotation of the guiding cannula 16 within portal cannula 13 from the lowermost position shown to a position shown in phantom in FIG. 5B would provide the conically shaped field of view 71 shown in dotted lines. Maintaining the guiding cannula 16 in this position and rotating the bendable scope 18 by 180° within the guiding cannula 16 as previously explained would then provide the conically shaped field of view 73 shown in solid lines. As is apparent depending on the orientation of the bendable scope 18 and guiding cannula 16 a full hemispherically shaped field of view 61 can be provided.

Thus the invention provides a scope assembly for flexible endoscopes capable of a full hemispherically shaped field of view. While the particular flexible endoscope as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A scope assembly for an endoscope for examining an internal structure of a body, which comprises:
    a substantially rigid guiding cannula removably attached to the endoscope, said guiding cannula having a substantially straight longitudinal axis and having a distal end bent at a first angle relative to said longitudinal axis, said guiding cannula being adapted for rotation within a stationary portal cannula adapted to be inserted into the body, thereby rotating said bent distal end through an arc about the axis of said portal cannula;
    a flexible scope removably attached to the endoscope, said scope being slidable and rotatable within said guiding cannula, and said scope including an illuminating means for directing light into the body and a flexible image guide for gathering reflected light from the body;
    a distal viewing end on said image guide, said viewing end being constrained by said bent distal end of said guiding cannula to offset the axis of said viewing end, at said first angle relative to said longitudinal axis; and
    a lens mounted on said distal viewing end of said image guide, said lens having an optical axis offset at a second angle relative to said axis of said viewing end.

2. The scope assembly as defined in claim 1 and wherein the distal end of said scope extends axially past said bent distal end of said guiding cannula.

3. The scope assembly as defined in claim 2 and wherein said lens is adapted to provide a generally conically shaped field of view.

4. The scope assembly as defined in claim 3 and wherein said conically shaped field of view has a total conical angle of about 70 degrees.

5. The scope assembly as defined in claim 4 and wherein said first angle is about 30 degrees.

6. The scope assembly as defined in claim 5 and wherein said second angle is about 25 degrees.

7. A scope assembly for an endoscope for viewing an internal structure of a body comprising:
    a stationary portal cannula adapted to be inserted into the body at a site to be examined;
    a disposable rigid guiding cannula detachably mounted to the endoscope, said guiding cannula adapted to be rotated within said portal cannula, and said guiding cannula having a straight longitudinal axis and an open distal end bent along a distal axis relative to said longitudinal axis;
    a disposable bendable scope detachably mounted to the endoscope and rotatable within said guiding cannula, said bendable scope having a distal viewing end constrained by said guiding cannula to bend along said distal axis, and said scope including an illuminating means and an image guide; and
    a viewing lens mounted on said image guide at said distal viewing end of said scope, said viewing lends having an optical axis offset relative to said distal axis for gathering light from said illuminating means for generating a visual image of the internal structure of the body illuminated by said illuminating means.

8. The scope assembly as defined in claim 7 and wherein said viewing lens of said image guide extends axially past said distal end of said guiding cannula.

9. The scope assembly as defined in claim 8 and wherein rotation of said guiding cannula relative to said portal cannula, combined with rotation of said bendable scope relative to said guiding cannula, rotates said viewing lens to provide a generally hemispherically shaped field of view.

10. The scope assembly as defined in claim 9 and wherein said distal axis of said guiding cannula is formed at an angle of about thirty degrees relative to said longitudinal axis.

11. The scope assembly as defined in claim 10 and wherein said viewing lens has a generally conical shaped field of view with a conical angle of about 70 degrees.

12. The scope assembly as defined in claim 11 and wherein said optical axis of said viewing lens is at an angle of about twenty-five degrees with said distal axis of said guiding cannula.

13. The scope assembly as defined in claim 12 and wherein said guiding cannula is detachably mounted to the endoscope using a clamp-like connector.

14. A scope assembly for an endoscope for viewing an internal structure of a body comprising:
    a stationary portal cannula adapted to be inserted into the body at a site to be examined;
    a disposable rigid guiding cannula detachably mounted to a housing of the endoscope, said guiding cannula having a straight longitudinal axis and a straight distal end offset from said longitudinal axis along a distal axis, said guiding cannula being adapted to be rotated within said portal cannula by manipulation of the housing;
    a disposable bendable scope detachably mounted to the housing and rotatable within said guiding cannula by manipulation of said bendable scope, with said bendable scope having a viewing end extending from said distal end of said guiding cannula, said viewing end being constrained by said distal end of said guiding cannula to bend along said distal axis;
    an image guide mounted within said bendable scope; and
    a GRIN rod lens mounted at a distal end of said image guide with said GRIN rod lens having an optical axis offset from said distal axis of said guiding cannula to form an offset viewing axis so that rotation of said guiding cannula within said portal cannula, combined with rotation of said bendable scope within said guiding cannula, moves said GRIN rod lens through a generally hemispherically shaped field of view.

15. The scope assembly as recited in claim 14 and wherein said GRIN rod provides a generally conical shaped field of view and said distal axis of said guiding cannula forms an angle of about 30 degrees with said longitudinal axis.

16. The scope assembly as recited in claim 15 and wherein said viewing axis forms an angle of about 25 degrees with said distal axis of said guiding cannula.

17. The scope assembly as recited in claim 16 and wherein said bendable scope is bent only at a distal end.

18. The scope assembly as recited in claim 16 and wherein said bendable scope is formed of a material that is flexible but solid.

19. The scope assembly as recited in claim 16 and wherein said scope assembly is part of an arthroscope.

20. The scope assembly as recited in claim 19 and wherein said arthroscope is portable and can be hand held.

* * * * *